United States Patent [19]
McIntosh et al.

[11] Patent Number: 6,097,484
[45] Date of Patent: Aug. 1, 2000

[54] LOCATION OF DEFECTS USING DYE PENETRATION

[75] Inventors: John M. McIntosh, Orlando; Brittin C. Kane, Clermont; Annette M. Crevasse; Todd C. Henry, both of Orlando, all of Fla.

[73] Assignee: Lucent Technologies, Inc., Murray Hill, N.J.

[21] Appl. No.: 09/353,860

[22] Filed: Jul. 15, 1999

[51] Int. Cl.[7] .......................... G01N 21/00; G01N 31/00
[52] U.S. Cl. .................... 356/237.5; 356/237.2; 356/237.1; 436/5; 436/172
[58] Field of Search ............... 356/237.1, 237.2, 356/237.3, 237.4, 237.5; 436/5, 172

[56] References Cited

U.S. PATENT DOCUMENTS 5,965,446  10/1999  Ishikawa ........................ 356/237.1

*Primary Examiner*—Hoa Q. Pham
*Assistant Examiner*—Roy M. Punnoose
*Attorney, Agent, or Firm*—Quarles & Brady LLP

[57] ABSTRACT

A method for amplifying defects connected to a top surface of a semiconductor device comprises the steps of applying a dye, removing the dye, and applying a developing gel. The dye enters into defects connected to the top surface of the semiconductor device. After removal of the dye from the top surface and application of the developing gel, the dye contained within the defects leaches into the developing gel to form defect indications. These defect indications have a better optical visibility than the defects themselves. An apparatus for performing this method is also disclosed.

14 Claims, 4 Drawing Sheets

LOCATION OF DEFECTS USING DYE PENETRATION

CROSS-REFERENCE TO RELATED APPLICATION

Not Applicable

STATEMENT REGARDING FEDERALLY SPONSORED RESEARCH AND DEVELOPMENT

Not Applicable

FIELD OF THE INVENTION

This invention relates to locating defects during semiconductor manufacturing. More specifically, the invention relates to a method and device for finding surface and subsurface defects on wafers using dye to amplify the size of the defects.

BACKGROUND OF THE INVENTION

The detection of defects on wafers is of particular interest to the semiconductor industry. In many instances, a defect in a wafer, if uncorrected, can cause the failure of the final product, an integrated circuit (IC) chip. Identifying the defect during processing is particularly valuable for several reasons. For example, if the defects were discovered during one step of the processing, it is possible that the wafer could be reworked to eliminate the defect(s). Additionally, even if the wafer could not be reworked, identifying the location and frequency of the defects will provide important information regarding the repeatability and quality of the previous processes. This information can then be used to makes changes to the previous processes so as to minimize the defects.

Not only is location and frequency important data to collect regarding defects, the characterization of the defects is also important. After determining what defects are present, it can be determined how that particular defect was created. For example, chemical metal planarization (CMP) causes many types of defects. These defects include surface defects, embedded defects, and microscratches. Surface defects can be the result of residual material, which can include material from the polishing pad, slurry, residual tungsten, titanium or titanium oxide. Therefore, by characterizing the defect after a particular process, for example CMP, it can be determined how the defect was created.

A particularly serious defect is an embedded particle in an oxide that the CMP process rips out thereby leaving a void in the oxide. This void could subsequently be filled with tungsten or another metal and not removed by a later CMP process. This puddle of metal could then result in a die-killing short circuit at subsequent metal levels.

Other types of defects exist during the processing of semiconductor wafers. Common defects are unfilled vias or windows and deviations in the via top profile. Unfilled vias have many causes including the metal being pulled out during the CMP process or the filling of the via may have been blocked by a particle. Deviations in the via top profile can be caused due to local arcing or cratering.

Two types of equipment are commonly used to locate these types of defects. The typical procedure is to inspect the wafer for defects with an optical comparitor tool. Once the locations of defects are determined, the locations are given to another tool, which will characterize the defect. Two such tools used for characterization of defects are an optical inspection tool or a scanning electron microscope (SEM). The advantage of using an optical inspection tool is its ability to position itself to the defect and quickly focus on the defect. However, an optical inspection tool has difficulty distinguishing between a surface defect and a void at high magnification levels of approximately 0.25 micros per pixel. As the features become smaller than 0.25 microns, the wavelength of the light reflected from defects of similar size is not long enough for the optical inspection tool to characterize the defect.

Alternatively, the defects can be characterized using a SEM. However, use of a SEM presents different problems. A SEM cannot easily focus on a substantially flat oxide film. Also, throughput (i.e., the number of inspections during a given period of time) of an SEM is much smaller than the throughput of an optical inspection tool. With the throughput of an SEM being so low, the use of a SEM during manufacturing is typically considered not feasible. Thus, as the size of features becomes smaller and the size of defects to be detected also becomes smaller, the current devices and methods of detecting these defects are inadequate.

Another problem associate with current inspection methods are their vulnerability to "noise". One type of noise that affects current inspection methods is from the underlying metal pattern or from the metal grain in the situation of large metal areas. Another type of noise is color noise originating from the variation of oxide film thickness across the wafer and from die to die.

SUMMARY OF THE INVENTION

It is therefore an object of-the invention to provide a method and device for detecting surface and subsurface defects on a semiconductor wafer.

It is another object of the invention to provide a method and device for detecting surface and subsurface defects that are less than 0.25 microns.

It is yet another object of the invention to provide a method and device for detecting surface and subsurface defects that uses optical methods to detect the defects.

It is still another object of the invention is to provide a method and device for detecting surface and subsurface defects which are not susceptible to noise caused by the underlying metal pattern or from the metal grain or color noise originating from the variation of oxide film thickness across the wafer and from die to die.

These and other objects of the invention are achieved by the subject method which comprises the steps of applying a dye, removing the dye, and applying a developing gel. Upon application of the dye, the dye enters defects connected to the top surface of the semiconductor device. After removal of the dye from the top surface and application of the developing gel, the dye contained within the defects leaches into the developing gel to form defect indications. These defect indications have a better optical visibility than the defects themselves.

A second embodiment of the invention is an defect amplifier which comprises a dye applicator, a dye remover, and a gel applicator. The dye applicator applies a layer of dye to a top surface of the semiconductor device. Upon application of the dye onto the top surface, the dye enters into the defects. The dye remover removes the remaining dye from the top surface. The gel applicator then applies a layer of developing gel to the top surface. The dye then leaches from the defects into the developing gel to form defect indications.

A heater can be provided to heat the developing gel so as to increase the leaching rate of the dye into the developing gel. Also, an optical reader can be provided for reading the defect indications. In a preferred embodiment, both the dye applicator and gel applicator are spin coaters.

BRIEF DESCRIPTION OF THE DRAWINGS

There are shown in the drawings embodiments of the invention that are presently preferred, it being understood, however, that the invention is not limited to the precise arrangements and instrumentalities shown. Specifically.

FIG. 1 shows a layer having defects such as a crack, partial void, and void.

FIG. 2 shows the layer of FIG. 1 after the application of dye onto the top surface of the layer.

FIG. 3 shows the layer of FIG. 2 after the dye has been removed from the top surface of the layer.

FIG. 4 shows the layer of FIG. 3 after a developing gel has been applied to the top surface of the layer.

FIG. 5 shows the layer of FIG. 4 after the dye has been leached into the developing gel.

DETAILED DESCRIPTION OF THE PREFERRED EMBODIMENTS

Figure 1:
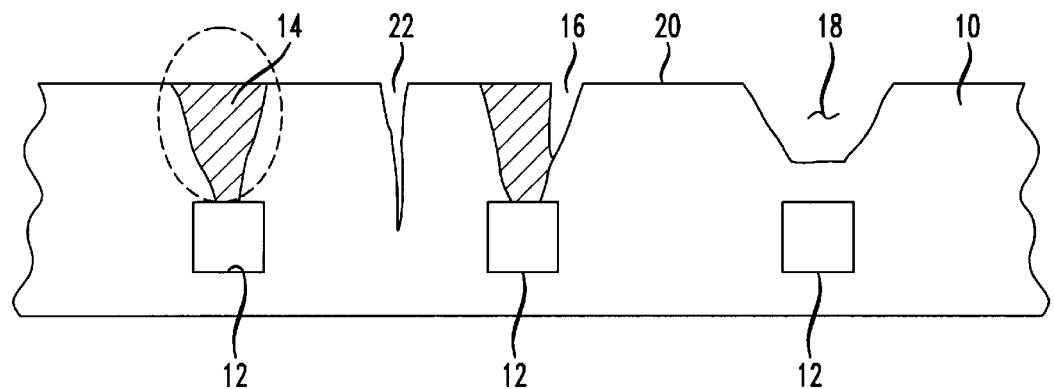
FIGS. 1 through 5 are side cross-sectional views illustrating one sequence of steps involved in the method of detecting surface and subsurface defects on a semiconductor wafer.

Referring to FIGS. 1 through 5, a method for amplifying surface and subsurface defects in a semiconductor wafer according to the present invention is illustrated. FIG. 1 illustrates a layer 10 of a semiconductor wafer to be examined. Layers 10 of semiconductor wafers can be formed from many different materials, and this invention is not limited as to be used with a particular type of material. A typical material used for a layer 10 is an oxide, for example, a silicon oxide.

Also illustrated are typical features found in a layer such as metal 12 and vias or windows 14 connected to the metal 12. The windows 14 are typically filled with a conductive material, for example tungsten or copper, to electrically connect the metal 12 to the next layer. A completely filled window 14 is circled in phantom. However, a window 14 that is not completely filled or completely created may generate a defect. One such defect is a partial void 16. A partial void 16 can be created by many reasons, for example, the window 14 may not have been completely filled during deposition or the CMP process may have pulled out a portion of the window 14.

Another type of defect is a void 18. As with the partial void 16, a void 18 can be the result of incomplete filling of the window 14 or the pulling out of a portion of the window 14. However, the void 18 does not necessarily have to be associated with a window 14. The void 18 can be created anywhere along the top surface 20 of the layer 10.

Still another type of defect associated with semiconductor manufacturing is a crack 22. Other types of surface and subsurface defects are also well known in semiconductor manufacturing. The aforementioned defects are only intended to be illustrative of the types of defects present during semiconductor manufacturing and are not intended to limit the present invention in any manner.

Figure 2:
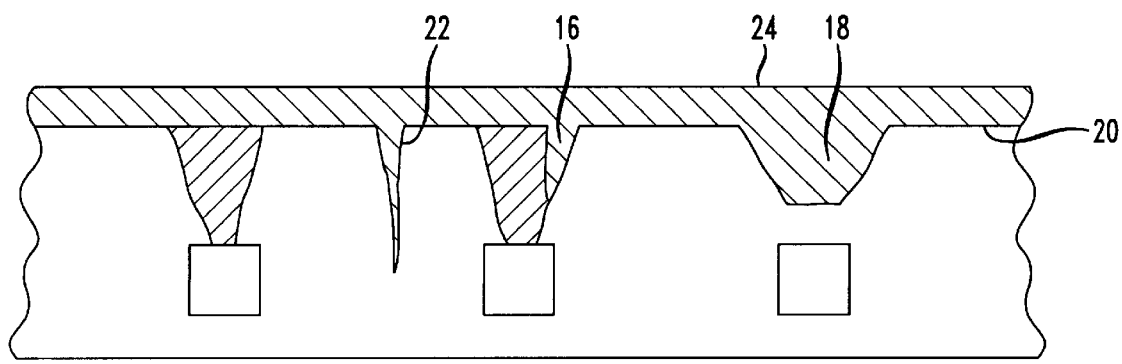

FIG. 2 illustrates the application of the penetrant dye 24 onto the top surface 20 of the layer 10. The penetrant dye 24 acts to penetrate into defects, such as cavities or recesses, connected to the top surface 20. Examples of these cavities or recesses are cracks 22, partial voids 16, and voids 18. It being understood that the penetrant dye 24 is not limited to penetration into cracks 22, partial voids 16, and voids 18, but will penetrate into any cavity or recess connected to the top surface 20.

Penetrant dyes 24 are known in the art, and this invention is not limited as to a particular type of penetrant dye 24. Penetrant dyes 24 can have many different qualities, for example, the penetrant dye 24 can be fluorescent to aid in the detection of a defect. Also, the penetrant dye 24 can be optically reflective at different wavelengths of light.

Any method or device of applying the penetrant dye 24 to the top surface 20 of the layer 10 is acceptable so long as the penetrant dye 24 completely covers the surface area to be examined. The presently preferred device for applying the penetrant dye 24 to the top surface 20 is a spin coater. A spin coater is known in the art and is used with other semiconductor manufacturing processes to apply an uniform film of liquid to the top surface 20 of a wafer.

Figure 3:
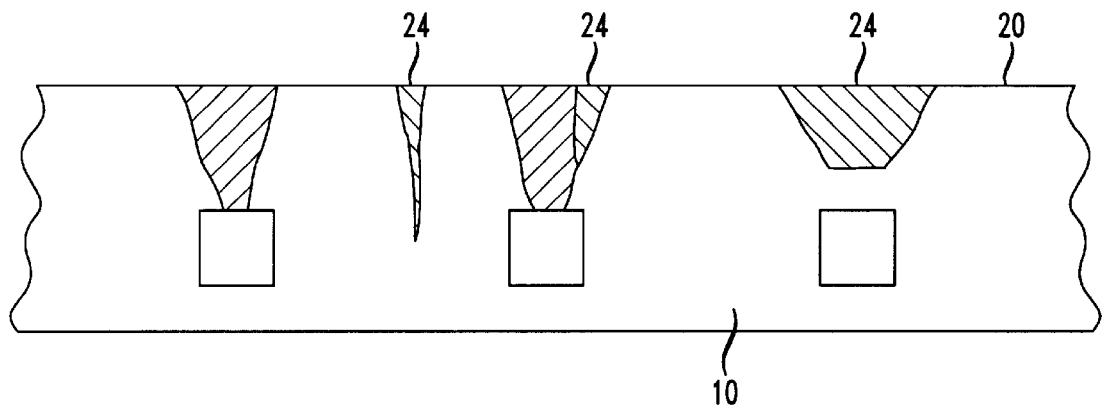

After the penetrant dye 24 has been allowed to penetrate into the cavities and recesses, FIG. 3 illustrates the layer 10 after the penetrant dye 24 disposed on the top surface 20 of the layer 10 has been removed. It is noted that the penetrant dye 24, although removed from the top surface 20, still remains in any cavities or recesses connected to the top surface 20, for examples cracks 22, partial voids 16, and voids 18. The penetrant dye 24 can remain in the cavities and recesses by surface tension, for example.

The method or device used to remove the penetrant dye 24 from the top surface 20 of the layer 10 preferably does not remove the penetrant dye 24 from the cavities or recesses. Such methods or devices are commonly known, and all so capable are acceptable for use with the present invention.

Figure 4:
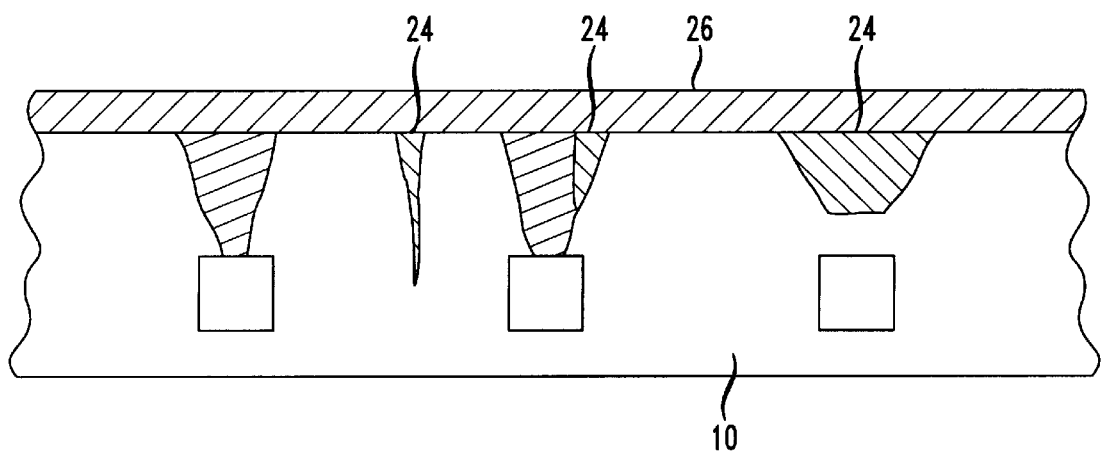
Figure 5:
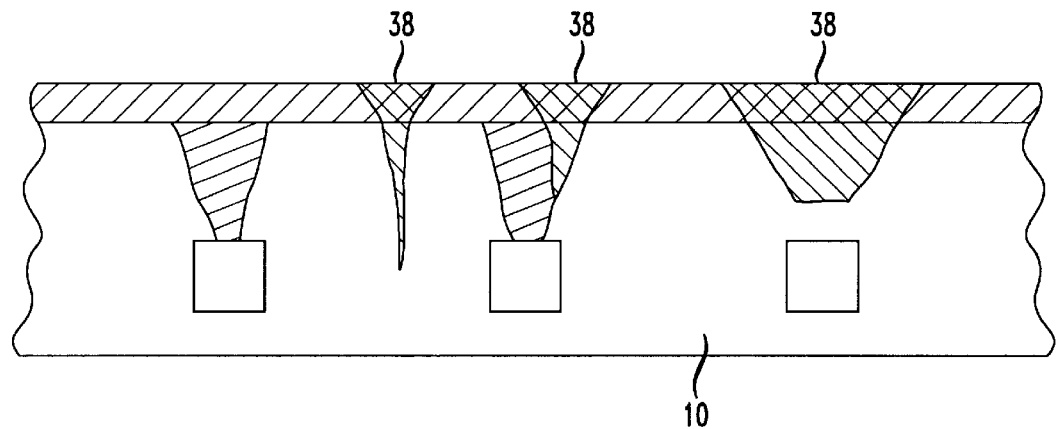

Once the penetrant dye 24 has been removed from the top surface 20, FIG. 4 illustrates the layer 10 after a developing gel 26 has been applied to the top surface 20. The function of the developing gel 26 is to absorb the penetrant dye 24 contained with the cavities or recesses. Many types of developing gels 26 are known in the art, and any developing gel 26 capable of absorbing the penetrant dye 24 is acceptable for use with the present invention. However, penetrant dye systems typically include both a penetrant dye 24 and a developing gel 26 with the developing gel 26 specifically tailored to be used with the penetrant dye 24. As such, selection of both the penetrant dye 24 and developing gel 26 will preferably be done in combination.

One presently preferred characteristic of the penetrant dye system is that a bright contrast exists between the developing gel 26 and the developing gel 26 after absorption of penetrant dye 24. This bright contrast allows for better optical identification of those defect indications 38 in which the developing gel 26 has absorbed the penetrant dye 24. Also, a penetrant dye system can be selected so that application of heat to the developing gel 26 can increase the diffusion rate of the penetrant dye 24 into the developing gel 26. Advantageously, this characteristic allows for quicker optical identification of the defects after the developing gel 26 has been applied to the top surface 26.

As with the application of the penetrant dye 24 onto the top surface 20, any method or device of applying the developing gel 26 to the top surface 20 of the layer 10 is acceptable so long as the developing gel 26 completely covers the surface area to be examined. The presently preferred device for applying the developing dye 26 to the top surface 20 is a spin coater.

Figure 6:
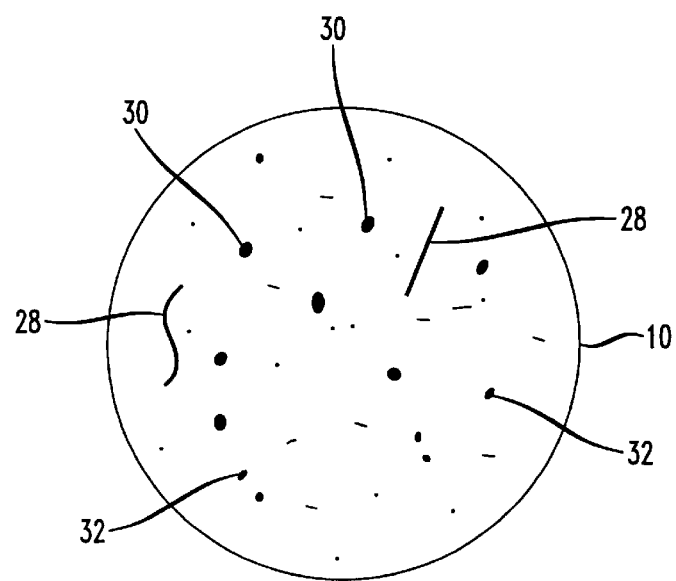
FIG. 6 shows a top plan view of FIG. 5 illustrating the different patterns exhibited by different types of defect indications.

FIG. 6 illustrates various defect indications 38 in the developing gel. A defect indication 38 is the dye stain related to defect. Each type of defect will have a characteristic defect indication pattern and size. For example, a crack can be indicated a line 28 having a length significantly greater than its width. A large defect, such as a void, can be indicated by a substantial circular large mark 30, and a partial void can be indicated by a smaller mark 32. It should be noted that other defects may exhibit other characteristic defect indication patterns and sizes, and this invention is not limited as to indicating a particular type, pattern, or size of defect.

Figure 7:
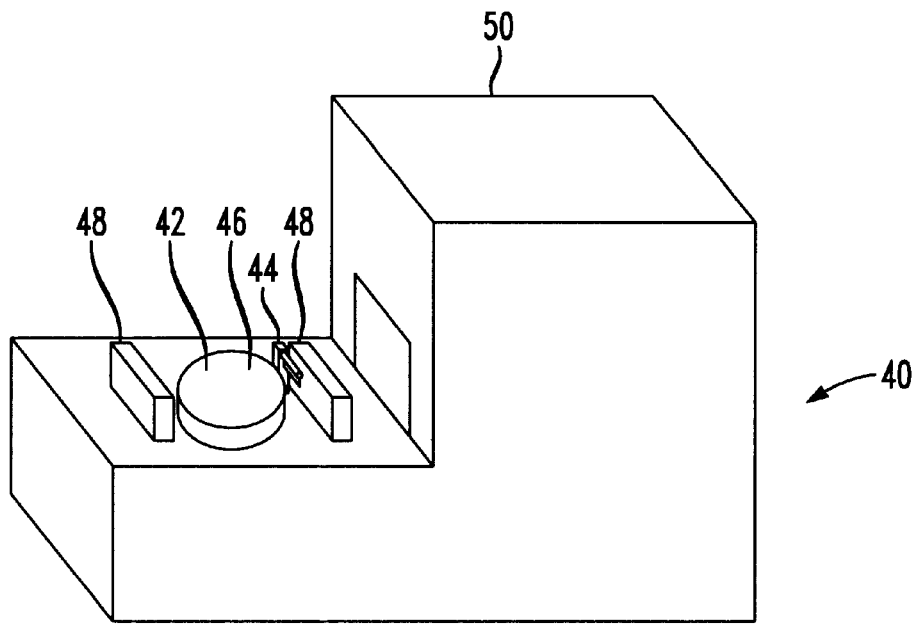
FIG. 7 is a perspective view of a defect amplifier for amplifying defects on a semiconductor device according to an embodiment of the invention.
Figure 8:
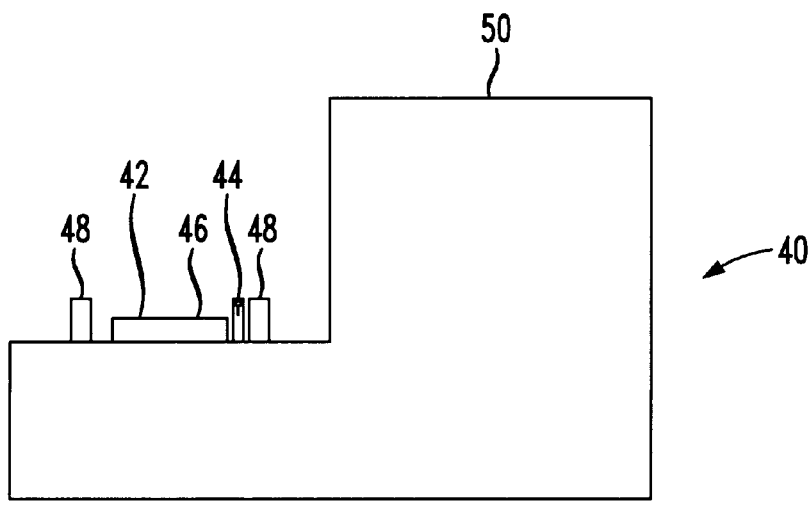
FIG. 8 is a side view of the defect amplifier as illustrated in FIG. 7.

A device for amplifying and detecting defects according to present invention is illustrated in FIGS. 7 and 8. The defect amplifier 40 comprises a dye applicator 42, a dye remover 44, a gel applicator 46, a heater 48, and an optical reader 50. Although the presently preferred embodiment of the defect amplifier 40 includes the optical reader 50, the optical reader 50 can be separate from the defect amplifier 40.

The dye applicator 42 acts to apply a layer of penetrant dye over those areas of the wafer to be inspected. As previously stated, any dye applicator 42 capable of applying a layer of penetrant dye onto the wafer to be inspected is acceptable for use in the present invention. However, the presently preferred dye applicator 42 is a spin coater. A spin coater advantageously is already being used in the processing of semiconductor wafers and is capable of applying a thin, constant-thickness layer of fluid onto the surface of a wafer.

The dye remover 44 acts to remove the penetrant dye from the surface of the wafer without removing the penetrant dye contained with the cavities or recesses connected to the surface. As previously stated, any dye remover 44 capable of removing the penetrant dye from the surface of the wafer without removing the penetrant dye contained with the cavities or recesses connected to the surface is acceptable for use in the present invention. However, the presently preferred dye applicator 42 is a bladed squeegee.

The gel applicator 46 acts to apply a layer of developing gel over those areas of the wafer to be inspected. As previously stated, any gel applicator 46 capable of applying a layer of developing gel onto the wafer to be inspected is acceptable for use in the present invention. However, the presently preferred gel applicator 46 is a spin coater. As advantageously used with applying the penetrant dye, the spin coater is used to apply a thin, constant-thickness layer of developing gel onto the surface of a wafer. In the preferred embodiment, the spin coater used for the dye applicator 42 is the same spin coater used for the gel applicator 46.

A heater 48 can optionally be provided to increase the diffusion rate of the penetrant dye into the developing gel as previously discussed. Heaters 48 are well known in the art and any heater capable of providing a desired amount of heat to the developing gel is acceptable for use with the present invention.

The optical reader 50 is used to identify and characterize the defects revealed by the defect indications on the developing gel. Optical readers 50 are well known in the art, and this invention is not limited as to a particular optical reader 50. As previously stated, the optical reader 50 can be integral with the defect amplifier 40. Alternatively, the optical reader 50 can be separate for the defect amplifier 40 with the wafer being subsequently moved from the defect amplifier 40 to the optical reader 50 after the defect amplifier 40 has amplified the defects on the wafer.

It should be understood that the examples and embodiments described herein are for illustrative purposes only and that various modifications or changes in light thereof will be suggested to persons skilled in the art and are to be included within the spirit and purview of this application. The invention can take other specific forms without departing from the spirit or essential attributes thereof for an indication of the scope of the invention.

What is claimed is:

1. A method for amplifying defects connected to a top surface of a semiconductor device, comprising the steps of:

applying dye to the top surface, the dye on the top surface thereby entering and being captured by the defects;

removing the dye from the top surface; and, applying developing gel to the top surface to leach the dye from the defects into the developing gel, the leaching of the dye into the developing gel forming a defect indication.

2. A method for amplifying defects according to claim 1, further comprising the step of inspecting the top surface for the defect indications.

3. A method for amplifying defects according to claim 2, wherein said dye is fluorescent.

4. A method for amplifying defects according to claim 3, further comprising the step of applying fluorescent light to the top surface during said inspecting step.

5. A method for amplifying defects according to claim 2, further comprising the step of characterizing the defects after said inspection step.

6. A method for amplifying defects according to claim 2, wherein the inspection is optical.

7. A method for amplifying defects according to claim 1, further comprising the step of heating the developing gel.

8. A method for amplifying defects according to claim 1, wherein the defects are less than 0.25 microns.

9. A method for amplifying defects less than 0.25 microns connected to a top surface of a semiconductor device, comprising the steps of:

applying fluorescent dye to the top surface, the dye on the top surface thereby entering and being captured by the defects;

removing the dye from the top surface;

applying developing gel to the top surface to leach the dye from the defects into the developing gel, the leaching of the dye into the developing gel forming a defect indication;

heating the developing gel to increase the rate of leaching;

concurrently applying fluorescent light to the top surface and inspecting the top surface for the defect indications; and, characterizing the defect indications.

10. A defect amplifier for amplifying defects connected to the top surface of a semiconductor device, comprising:

a dye applicator for applying dye to the top surface, the dye thereby entering into the defects;

a dye remover for removing the dye from the top surface;

a gel applicator for applying developing gel to the top surface, the dye leaching from the defects into the developing gel to form defect indications.

11. The defect amplifier of claim 10, further comprising an optical reader for reading the defect indications.

12. The defect amplifier of claim 10, further comprising a heater for heating the developing gel.

13. The defect amplifier of claim 10, wherein the dye applicator is a spin coater.

14. The defect amplifier of claim 10, wherein the gel applicator is a spin coater.

* * * * *